United States Patent
Ding et al.

(10) Patent No.: US 9,862,720 B2
(45) Date of Patent: Jan. 9, 2018

(54) INHIBITORS OF THE RENAL OUTER MEDULLARY POTASSIUM CHANNEL

(71) Applicant: Merck Sharp & Dohme Corp., Rahway, NJ (US)

(72) Inventors: Fa-Xiang Ding, Staten Island, NY (US); Shuzhi Dong, Plainsboro, NJ (US); Jinlong Jiang, Scotch Plains, NJ (US); Takao Suzuki, Shanghai (CN); Joseph P. Vacca, Telford, PA (US); Shouning Xu, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/505,620

(22) PCT Filed: Oct. 26, 2015

(86) PCT No.: PCT/US2015/057280
§ 371 (c)(1),
(2) Date: Feb. 22, 2017

(87) PCT Pub. No.: WO2016/069427
PCT Pub. Date: May 6, 2016

(65) Prior Publication Data
US 2017/0283416 A1  Oct. 5, 2017

(30) Foreign Application Priority Data
Oct. 31, 2014  (WO) ................ PCT/CN2014/089999

(51) Int. Cl.
C07D 471/10 (2006.01)
A61K 31/435 (2006.01)
A61K 31/444 (2006.01)
A61K 31/501 (2006.01)

(52) U.S. Cl.
CPC .......... *C07D 471/10* (2013.01); *A61K 31/435* (2013.01); *A61K 31/444* (2013.01); *A61K 31/501* (2013.01)

(58) Field of Classification Search
None
See application file for complete search history.

(56) References Cited

U.S. PATENT DOCUMENTS

| | | |
|---|---|---|
| 2006/0252797 A1 | 11/2006 | Kajino et al. |
| 2014/0031349 A1 | 1/2014 | Ding et al. |
| 2014/0235628 A1 | 8/2014 | Walsh et al. |

FOREIGN PATENT DOCUMENTS

| | | |
|---|---|---|
| EP | 1329451 B1 | 8/2006 |
| WO | 2013062900 A1 | 5/2013 |
| WO | WO2016065603 A1 | 5/2016 |
| WO | WO2016069427 A1 | 5/2016 |

OTHER PUBLICATIONS

Bhave,G., Development of a selective small-molecule inhibitor Kir1.1, the renal outer medullary potassium channel, Mol. Pharmacol., 2011, 42-50, 79.
Fringuelli, F. et al., A Simple Procedure for the Synthesis of Labile Aryl Oxiranes by Epoxidation, Organic, Preparations and Procedures Int., 1989, p. 757-761, vol. 21, No. 6.
Hamill, O. P. et al., Improved Patch-Clamp Techniques for High-Resolution Current Recording from Cells and Cell-Free Membrane Patches, Pfugers Archiv—European Journal of Physiology, 1981, p. 85-100, vol. 391.
Hebert, S. C. et al., Molecular Diversity and Regulation of Renal Potassium Channels, Physiol Rev., 2005, p. 319-371, vol. 85.
Ho, K. et al., Cloning and expression of an inwardly rectifying ATP-regulated potassium channel, Nature, 1993, p. 31-38, vol. 362.
International Search Report and Written Opinion for PCT/US2015/057280, dated Jan. 14, 2016; 9 pages.
International Search Report of PCT/CN2014/089999 dated Aug. 10, 2015, pp. 14.
Ji, W. et al., Rare independent mutations in renal salt handling genes contribute to blood pressure variation, Nature Genetics, 2008, p. 592-599, vol. 40, No. 5.
Lerman, Lilach, O. et al., Animal Models of hypertension : An overview, J Lab Clin Med, 2005, p. 160-173, vol. 146, No. 3.
Lewis, L. M., High-throughput screening reveals a small-molecule inhibitor of the Renal Outer Medullary Potassium Channel and Kir7.1, Mol. Pharncol., 2009, 1094-1103, 76.
Lifton, R. P. et al., Molecular Mechanisms of Human Hypertension, Cell, 2001, p. 545-556, vol. 104.
Lorenz, J. N. et al., Impaired Renal NaCl Absorption inMic Lacking the ROMK Potassium Cannel, a Model for Type II Bartter's Syndrome, The Journal of Biological Chemistry, 2002, p. 37871-37880, vol. 277, No. 40.

(Continued)

*Primary Examiner* — Heidi Reese
(74) *Attorney, Agent, or Firm* — Baerbel R. Brown; Catherine D. Fitch

(57) ABSTRACT

The present invention provides compounds of Formula I and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

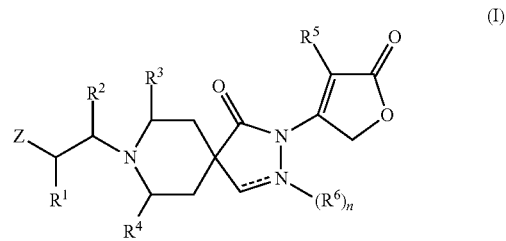

19 Claims, No Drawings

(56) References Cited

OTHER PUBLICATIONS

Lu, M. et al., Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37381-37887, vol. 277, No. 40.

Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.

Molander, G. A. et al., Suzuki-Miyaura Cross-Coupling Reactions of Potassium Vinyltrifluoroborate with Aryl and Heteroaryl Electrophiles, J. Org. Chem, 2006, p. 9861-9686, vol. 71.

Nomura, Y. et al., Synthesis and Structure-Activity Relationships of 2-(4-Benzhydryl-1-piperazinyl)-1-phenylethanols as New Calcium Blockers, Chem. Phar. Bull. 1995, p. 241-246, vol. 43, No. 2.

Reinalter, S. C. et al., Pharmacotyping of hypokalaemic salt-losing tubular disorders, Acta Physiol Scand, 2004, p. 513-521, vol. 181.

Shuck, M. E. et al., Cloning and Characterization of Multiple Forms of the Human Kidney ROM-K Potassium Channel, The Journal of Biological Chemistry, 1994, p. 24261-24270, Vo. 269, No. 39.

Tobin, M. D. et al., Common Variants in Genes Underlying Monogenic Hypertension and Hypotension and Blood Pressure in the General Population, Hypertension, 2008, p. 1658-1664, vol. 51. No. 6.

Wang, W. et al., Renal potassium channesl: recent developments, Current Opinion in Nephrology and Hypertension, 2004, p. 549-555, vol. 13, No. 5.

INHIBITORS OF THE RENAL OUTER MEDULLARY POTASSIUM CHANNEL

CROSS-REFERENCE TO RELATED APPLICATIONS

This application is a U.S. National Phase application under 35 U.S.C. §371 of PCT Application No. PCT/US2015/057280, filed on Oct. 26, 2015, which claims priority from and the benefit of Chinese PCT Patent Application PCT/CN2014/089999, filed Oct. 31, 2014.

FIELD OF THE INVENTION

The present invention relates to novel spirocyclic compounds and salts thereof useful as renal outer medullary potassium channel inhibitors. The present invention further relates to compositions containing such compounds, and methods of use thereof.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

Since then, other ROMK inhibitors have been described.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I:

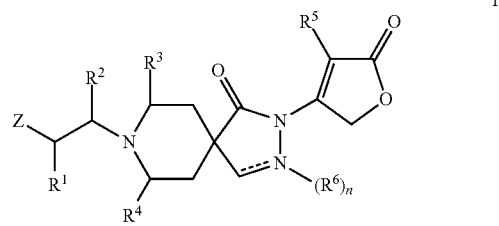

and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention addresses the following compounds, compounds of (1)-(19):

(1) A compound of Formula I:

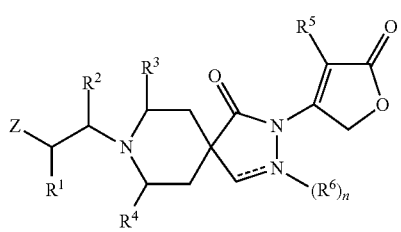

or a pharmaceutically acceptable salt thereof wherein:
$R^1$ is —H, —F, —OH, —$C_{1-3}$alkyl or —$OC_{1-3}$alkyl;
$R^2$ is —H, or $C_{1-4}$alkyl;
$R^3$ is —H, or —$C_{1-3}$alkyl optionally substituted with —OH, —$OCH_3$ or 1 to 3 of —F;
$R^4$ is —H, or —$C_{1-3}$alkyl optionally substituted with —OH, —$OCH_3$ or 1 to 3 of —F;
$R^5$ is —H, halo, —$C_{3-6}$cycloalkyl or —$C_{1-3}$alkyl;
$R^6$ is —H or —$C_{1-3}$alkyl when the dashed bond is absent, or $R^6$ is absent when the dashed bond is a double bond;
n is zero where $R^6$ is absent, or one where $R^6$ is present;
Z is

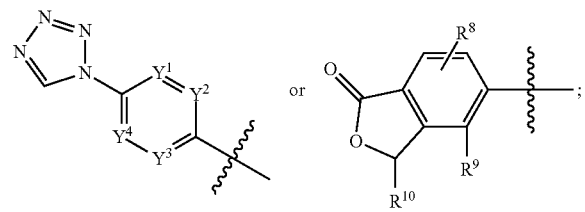

$Y^1$, $Y^2$, $Y^3$ and $Y^4$ are each independently selected from $C(R^7)$ or N;
provided that at most two of $Y^1$, $Y^2$, $Y^3$ and $Y^4$ are N;
each $R^7$ is independently —H, halo, $C_{1-4}$alkyl optionally substituted with 1-3 of —F, or $OC_{1-4}$alkyl;
$R^8$ is —H, halo, or $C_{1-4}$alkyl optionally substituted with 1-3 of —F;
$R^9$ is —H, $C_{1-4}$alkyl optionally substituted with 1-3 of —F, or halo; and
$R^{10}$ is —H or $C_{1-4}$alkyl.

(2) The compound of (1), or a pharmaceutically acceptable salt thereof, wherein $R^1$ is —H, —F or —OH.

(3) The compound of any of (1)-(2), or a pharmaceutically acceptable salt thereof, wherein $R^1$ is —OH.

(4) The compound of any of (1)-(3), or a pharmaceutically acceptable salt thereof, wherein $R^2$ is —H.

(5) The compound of any of (1)-(4), or a pharmaceutically acceptable salt thereof, wherein each of $R^3$ and $R^4$ are —H.

(6) The compound of any of (1)-(5), or a pharmaceutically acceptable salt thereof, wherein n is zero.

(7) The compound of any of (1)-(5), or a pharmaceutically acceptable salt thereof, wherein n is one and $R^6$ is —H or —$C_{1-3}$alkyl.

(8) The compound of any of (1)-(5), or a pharmaceutically acceptable salt thereof, wherein n is one and $R^6$ is —H.

(9) The compound of any of (1)-(8), or a pharmaceutically acceptable salt thereof, wherein $R^5$ is —H, —Cl, —$CH_3$ or cyclopropyl.

(10) The compound of any of (1)-(9), or a pharmaceutically acceptable salt thereof, wherein $R^5$ is —H.

(11) The compound of any of (1)-(9), or a pharmaceutically acceptable salt thereof, wherein $R^5$ is —$CH_3$.

(12) The compound of any of (1)-(11), or a pharmaceutically acceptable salt thereof, wherein Z is

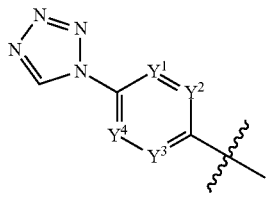

wherein each of the variables $Y^1$, $Y^2$, $Y^3$ and $Y^4$, and all other variables therein are as defined above in (1).

(13) The compound of any of (1)-(12), or a pharmaceutically acceptable salt thereof, wherein Z is

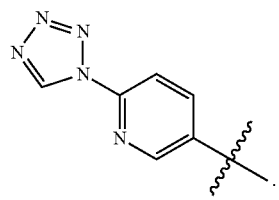 [SMILES: *c1ccc(-n2cnnn2)nc1]

(14) The compound of any of (1)-(12), or a pharmaceutically acceptable salt thereof, wherein Z is

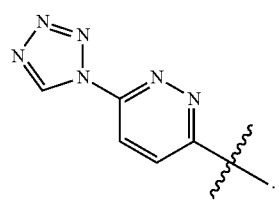 [SMILES: *c1ccc(-n2cnnn2)nn1]

(15) The compound of any of (1)-(11), or a pharmaceutically acceptable salt thereof, wherein Z is

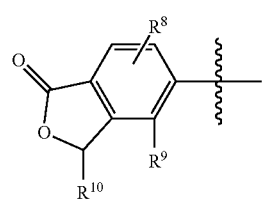

wherein each of the variables $R^8$, $R^9$ and $R^{10}$ are as defined above in (1).

(16) The compound of any of (1)-(11), or a pharmaceutically acceptable salt thereof, wherein Z is

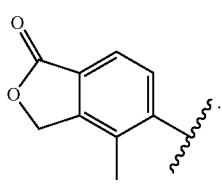 [SMILES: *c1ccc2c(c1C)COC2=O]

(17) The compound of any of (1)-(6) or (9)-(16) having structural Formula Ia or a pharmaceutically acceptable salt thereof:

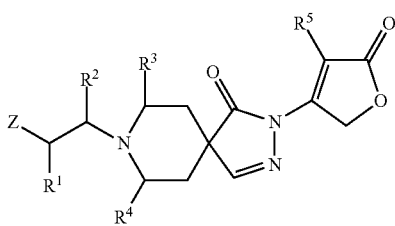

wherein each of the variables Z, $R^1$, $R^2$, $R^3$, $R^4$, and $R^5$, and all other variables therein are as defined in (1) or the appropriate embodiment.

(18) The compound of any of (1)-(5) or (7)-(16) having structural Formula Ib or a pharmaceutically acceptable salt thereof:

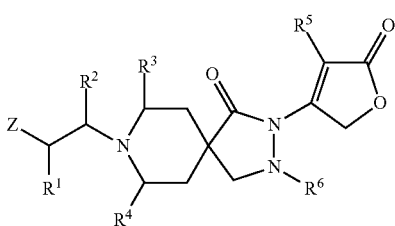

wherein each of the variables Z, $R^1$, $R^2$, $R^3$, $R^4$, $R^5$, and $R^6$, and all other variables therein are as defined in (1) or the appropriate embodiment.

(19) A compound of (1) which is:

8-(2-hydroxy-2-(4-methyl-1-oxo-1,3-dihydroisobenzofuran-5-yl)ethyl)-2-(4-methyl-5-oxo-2,5-dihydrofuran-3-yl)-2,3,8-triazaspiro[4.5]decan-1-one;

(R)-8-(2-hydroxy-2-(4-methyl-1-oxo-1,3-dihydroisobenzofuran-5-yl)ethyl)-2-(4-methyl-5-oxo-2,5-dihydrofuran-3-yl)-2,3,8-triazaspiro[4.5]decan-1-one [see Example 1];

8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one;

(R)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one [see Example 2A];

(S)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one [see Example 2B];

8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one;

(R)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one [see Example 3A];

(S)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one [see Example 3B];

8-(2-(6-(1H-tetrazol-1-yl)pyridazin-3-yl)-2-hydroxyethyl)-2-(4-methyl-5-oxo-2,5-dihydrofuran-3-yl)-2,3,8-triazaspiro[4.5]dec-3-en-1-one;

8-(2-(6-(1H-tetrazol-1-yl)pyridazin-3-yl)ethyl)-2-(4-methyl-5-oxo-2,5-dihydrofuran-3-yl)-2,3,8-triazaspiro[4.5]dec-3-en-1-one;

or a pharmaceutically acceptable salt thereof.

The compounds of the present invention are further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. Examples of alkyl groups include methyl, ethyl, propyl, isopropyl, butyl, sec- and tert-butyl, pentyl, hexyl, heptyl, octyl, nonyl and the like. In specific embodiments, alkyl means a linear or branched $C_{1-6}$ or $C_{1-3}$ alkyl.

"Alkoxy" refers to an alkyl group linked to oxygen. In specific embodiments, alkoxy means a linear or branched $C_{1-6}$ or $C_{1-3}$ alkoxy in which the point of attachment is at oxygen.

"Cycloalkyl" means a saturated cyclic hydrocarbon radical having the number of carbon atoms designated. Examples of cycloalkyl include cyclopropyl, cyclobutyl, cyclopentyl and cyclohexyl. In specific embodiments, cycloalkyl means a $C_{3-6}$ or $C_{3-4}$ cycloalkyl. In particular embodiments, cycloalkyl means $C_3$ cycloalkyl (or cyclopropyl).

"Halogen" or "halo" includes fluorine, chlorine, bromine and iodine.

Unless expressly depicted or described otherwise, variables depicted in a structural formula with a "floating" bond, such as substituent $R^8$, are permitted on any available carbon atom in the ring to which each is attached.

Substitution, where applicable, may be on any available carbon atom that results in a stable structure.

Also, number ranges where provided (e.g., 1-6) expressly include each and every number encompassed range and number as discrete embodiments. For example, "1-6" includes 1-6, 1-5, 1-4, 1-3, 1-2, 6, 5, 4, 3, 2 and 1 as distinct embodiments.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(19). For example, different isotopic forms of hydrogen (H) include protium (1H) and deuterium (2H). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(19) described herein can be prepared without undue experimentation by conventional techniques well known to those skilled in the art or by processes analogous to those described in the Examples herein using appropriate isotopically-enriched reagents and/or intermediates.

Individual tautomers of the compounds of any of (1)-(19), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(19) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(19) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(19) are also included in the present invention.

The term "pharmaceutically acceptable salt" refers to a salt prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In particular embodiments, the salt is selected from ammonium, calcium, magnesium, potassium, or sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of Formula I in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced unintended effects (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an IC50 of 5 µM or less, preferably 1 µM or less, and more particularly 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, particularly 0.001 to 30 mg/kg, in particular 0.001 to 10 mg/kg (in each case mg per kg of bodyweight) is appropriate for administration to an adult weighing approximately 75 kg in order to obtain the desired results. The daily dose is particularly administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, particularly mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; carbonic anhydrase inhibitors, such as acetazolamide; neutral endopeptidase inhibitors (e.g., thiorphan and phosphoramidon); angiotensin receptor neprilysin inhibitors (e.g., LCZ696); aldosterone antagonists; aldosterone synthase inhibitors; renin inhibitors (e.g., enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate), SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), SGLT2 inhibitors (e.g., canagliflozin, dapagliflozin, ipragliflozin, empagliflozin, tofogliflozin, luseogliflozin/TS-071, ertugliflozin, and remogliflozin), dipeptidyl peptidase inhibitors, (e.g., sitagliptin (JANUVIA®), omarigliptin, alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

EXAMPLES

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the the steps of reaction schemes may be varied to facilitate the reaction or to avoid unwanted reaction products. Unless specified otherwise, the "R", "Z", "Y" and "n" substituents in the Schemes correspond to the substituents defined in Formula I at the same positions on the structures.

Compound 1.3, which is substituted at the benzylic position with an OH group, can be prepared following the sequence detailed in Scheme 1. Coupling of epoxide 1.1 to spirocyclic amines 1.2 at elevated temperatures leads to the formation of alcohols 1.3 (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N,N-diisopropylethylamine may be added. Note that when enantiopure chiral epoxides are employed (such as (R)-1.1 in Scheme 1) epoxide opening occurs with retention of stereochemistry in the benzylic position and individual isomer (R)-1.3 may be obtained (and if the (S)-epoxide is employed the alcohol produced will have the opposite stereochemistry to that shown). Alternatively, chiral HPLC separation of enantiomers or diastereomers of 1.3 may be performed to provide single enantiomers or diastereomers.

SCHEME 1

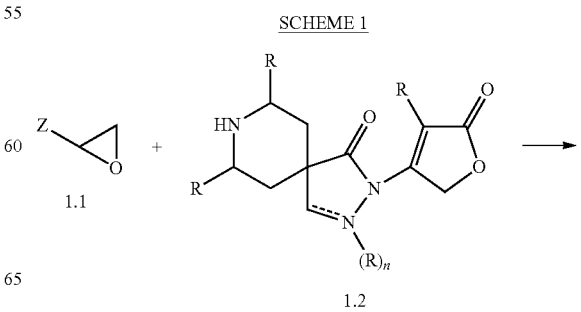

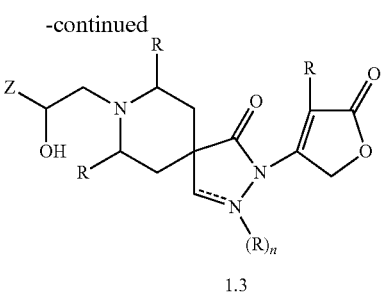

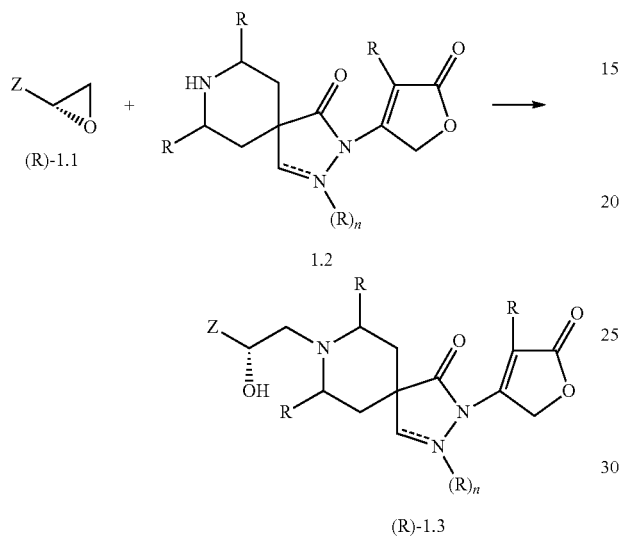

Compounds of formula 2.3 can be prepared by the sequence detailed in Scheme 2. Alhehydes or ketones 2.1 may be used in reductive alkylation reactions of spirocyclic amines 1.2 to afford ROMK inhibitors of the formula 2.3 by using various reductive amination conditions (for example using sodium cyanoborohydride, sodium triacetoxy borohydride, or titanium tetra-isopropoxide, followed by sodium borohydride or sodium cyanoborohydride). Alternatively, compounds of formula 2.3 can also be prepared by addition of amine 1.2 to an olefin of type 2.2 in the presence of a catalyst, e.g., $Rh(COD)_2BF_4$/DPEPhos. Under this condition, the olefins of type 2.2 may be required to be activated by a nitrogen atom or other electron-withdrawing group at the position ortho to the double bond.

Preparation of tetrazole styrene and tetrazole-epoxide intermediates of types 3.4 and 3.5 may start from halo-substituted aniline 3.1 (Scheme 3, X=halo). Thus, formation of the tetrazole ring can be accomplished by stirring $CF_3CO_2TMS$, $N_3TMS$ and $CH(OEt)_3$ in ethyl acetate or $NaN_3$ and $CH(OEt)_3$ in acetic acid at room temperature. The epoxide ring in intermediate 3.5 can be built by treatment of 3.2 (where X is chloride, bromide, iodide, or trifluoromethane sulfonate) with potassium vinyl trifluoroborate (Molander, G.; Luciana, A. Journal of Organic Chemistry, 2005, 70(10), 3950-3956) under palladium catalyzed coupling conditions followed by epoxidation of the formed styrene with NBS/NaOH. The intermediate styrene 3.4 can be used to prepare ROMK inhibitors in place of 2.2 according to Scheme 2. Other methods for formation of styrene may be employed, for example, using vinylstannane reagents and palladium catalysis, and other methods for epoxidation of the styrene may be used, for rexample, mCPBA. The racemic epoxides of formula 3.5 can be resolved under chiral HPLC chromatography conditions to afford its enantiomers (R)-3.5 and (S)-3.5, which can be used in place of 1.1 according to Scheme 1.

SCHEME 3

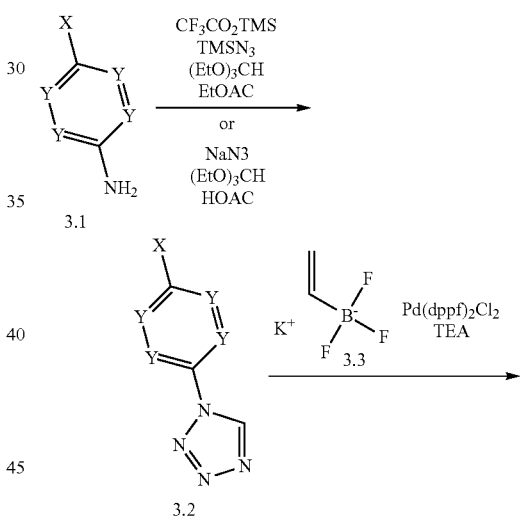

SCHEME 2

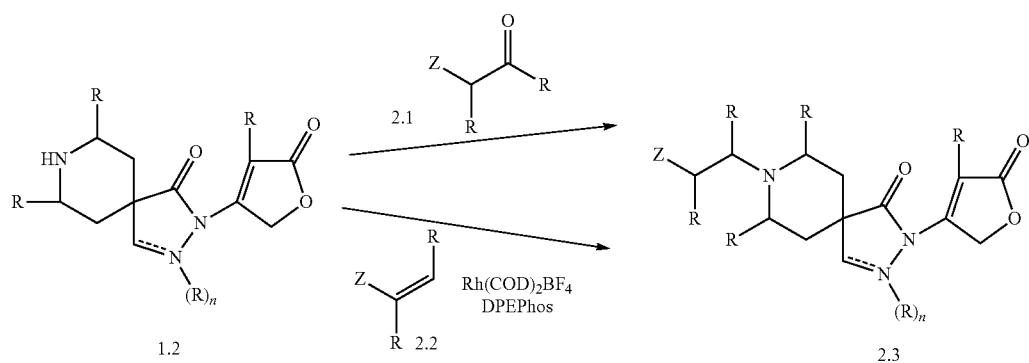

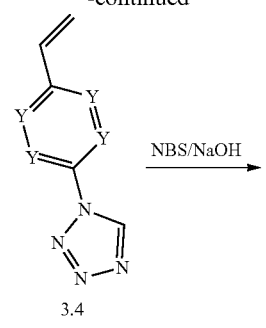

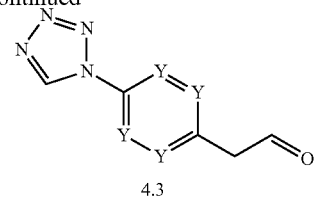

The epoxides 5.3 (and single enatiomers (R)-5.3 and (S)-5.3) can be prepared following the method detailed in Scheme 5. Treatment of 5.1 (where X is chloride, bromide, iodide, or trifluoromethane sulfonate) with commercially available potassium vinyl trifluoroborate (Molander, G.; Luciana, A. Journal of Organic Chemistry, 2005, 70(10), 3950-3956) under palladium catalyzed coupling conditions with an appropriate phosphine ligand gives rise to styrene 5.2 (Molander, G.; Brown, A. Journal of Organic Chemistry, 2006, 71(26), 9681-9686). Alternatively, other methods may be employed, for example, using vinylstannane reagents and palladium catalysis. The resulting styrenes 5.2 can be converted to the corresponding epoxides 5.3 under various epoxidation conditions, for example, with m-CPBA (Fringuelli, F. et al. Organic Preparations and Procedures International, 1989, 21(6), 757-761). The racemic epoxide 5.3 can be resolved under chiral HPLC chromatography conditions to afford its enantiomers (R)-5.3 and (S)-5.3), which can be used in place of 1.1 according to Scheme 1.

Aldehydes 4.3 can be prepared in numerous ways, including that described in Scheme 4. Aldehyde 4.3 can be prepared by hydrogenation of intermediate epoxides 3.5 followed by oxidation with Dess-Martin periodinane. Aldehydes 4.3 can be used in place of intermediates 2.1 in Scheme 2 to prepare ROMK inhibitors.

SCHEME 5

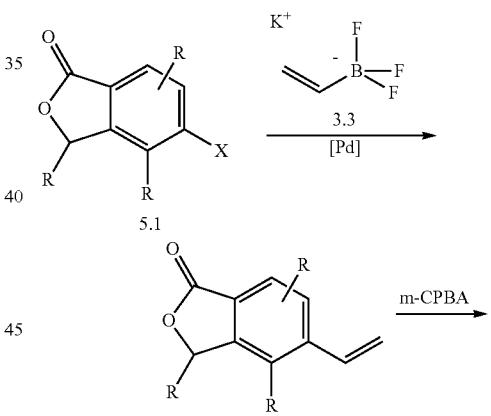

SCHEME 4

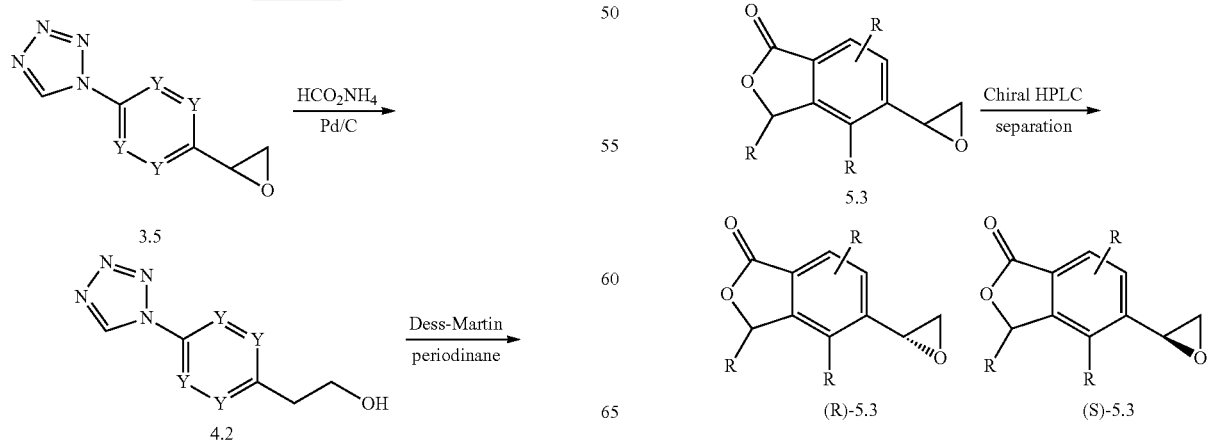

Alternatively, enantiopure epoxides (R)-5.3 or (S)-5.3 can be prepared as shown in Scheme 6. Treatment of 5.1 (where X is bromide, iodide, or trifluoromethane sulfonate) with commercial available vinyl butylether 6.1 under palladium catalyzed conditions with a suitable ligand (for example Pd(OAc)$_2$, DPPP) can provide the enol ethers 6.2. Enol ethers may be prepared using other methods known to the chemist. Treatment of the resulting enol ethers 6.2 with NBS or other similar reagents affords the corresponding bromomethyl ketones 6.3. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-5.3 or (S)-5.3 (depending upon the asymmetric reducing agent).

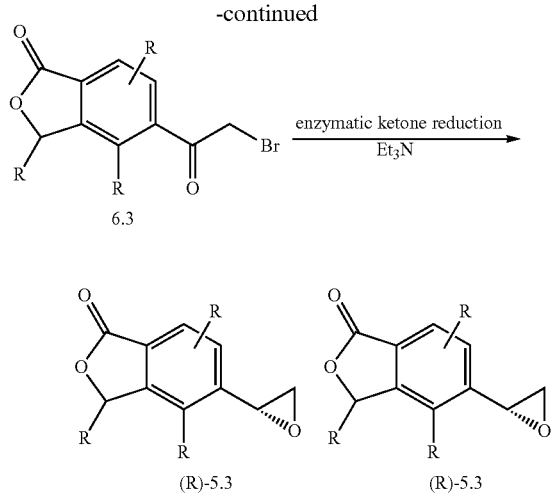

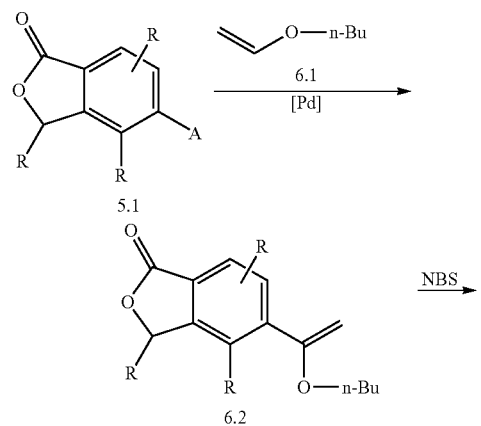

SCHEME 6

Aldehydes 7.2 may be prepared in numerous ways, with two approaches described in Scheme 7. Treatment of 5.1 (where X is bromide, iodide, or trifluoromethane sulfonate) with bromo(1,3-dioxolan-2-ylmethyl)zinc in the presence of an appropriate palladium catalyst and ligand, such as palladium(II) acetate and tri-t-butylphosphine-BF$_4$ complex, provides the corresponding aryl 1,3-dioxolan-2-ylmethyl derivative 7.1A. Then the aldehydes 7.2 may be obtained by treatment with HCl in the presence of water and an organic solvent. Alternatively, reaction of 5.1 (where X is bromide, iodide, or trifluoromethane sulfonate) with allyltributylstannane in the presence of palladium catalyst affords the allyl product 7.1. Oxidation, for example with ozone, followed by dimethyl sulfide, provides aldehydes 7.2.

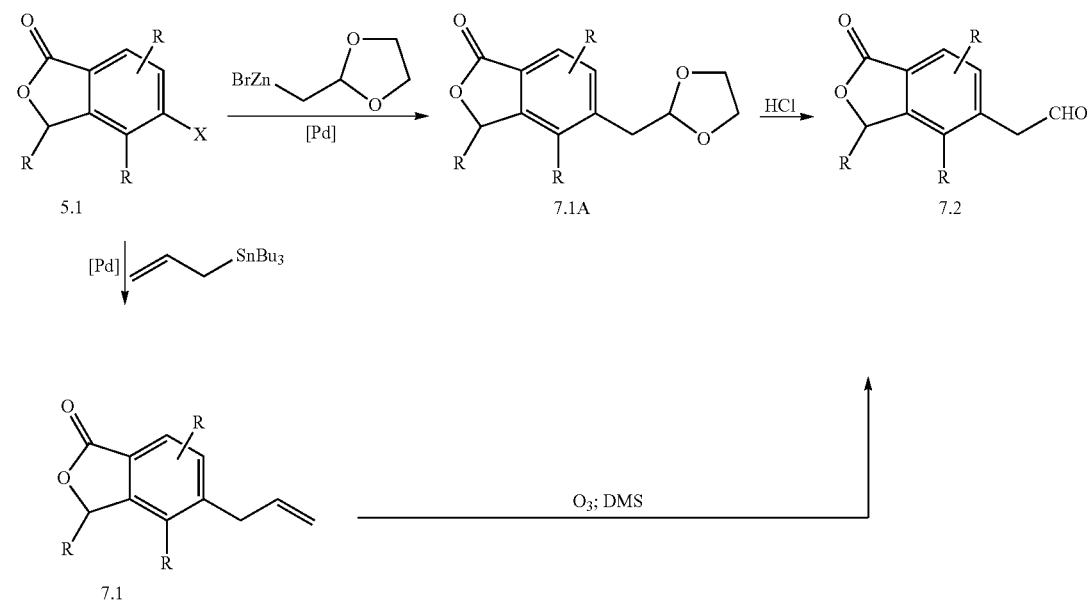

X = Br, OTf

Spirocyclic aminofuranones 8.4 can be prepared as described in Scheme 8. Spirocyclic diamines/amino lactams 8.1, where an amine is protected as appropriate (Greene, T.; Wuts, P. G. M. *protective Groups in Organic Synthesis*, John Wiley and Sons, Inc., New York, N.Y. 1991), can be coupled to furanone triflates or bromides 8.2 using a palladium catalyst and ligand, for example palladium acetate and 4,5-Bis(diphenylphosphino)-9,9-dimethylxanthene. Some spirocyclic diamines/amino lactams 8.1 described herein are commercially available; others can be prepared as described in the experimental section below. 4-Bromofuran-2(5H)-one is commercially available; other furanones 8.2 can be prepared as described in the examples below. Intermediates 8.3 are converted to spirocyclic aminofuranones 8.4 by removal of the protective group, for example, tert-butoxycarbonyl can be removed with TFA or HCl.

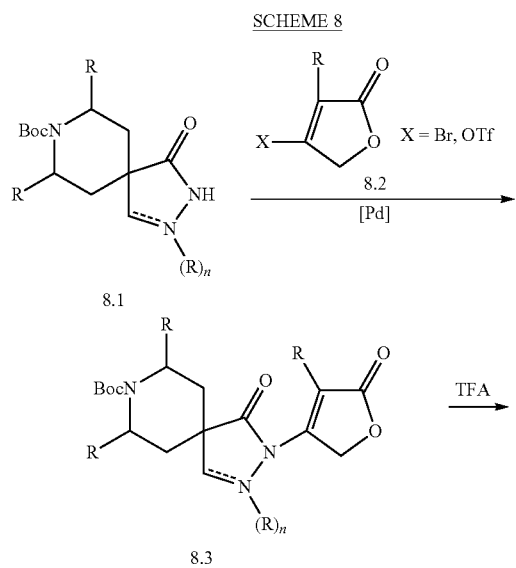

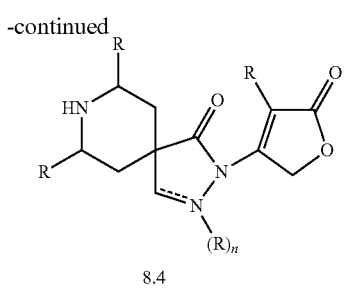

Methods for the synthesis of spirocyclic piperidines are detailed in the experimental section below. A general method for preparing spirocyclic piperidines 8.1A and 8.1B is depicted in Scheme 9 below. According to the Scheme, commercially available 1-tert-butyl 4-methyl piperidine-1, 4-dicarboxylate can be alkylated with diiodomethane after generation of the enolate with a base such as lithium diisopropylamide to provide iodomethyl intermediate 9.1. Treatment of 9.1 with hydrazine with warming then provides the spirocyclic piperidine 8.1A. Alternatively, 1-tert-butyl 4-methyl piperidine-1,4-dicarboxylate can be alkylated with paraformaldehyde after generation of the enolate with a base such as lithium diisopropylamide to provide hydroxymethyl intermediate 9.2. Oxidation of alcohol 9.2 to the corresponding aldehyde 9.3 can be achieved in a number of different ways, for example, by Swern oxidation conditions. Subsequent treatment of aldehyde 9.3 with hydrazine with warming provides spirocyclic piperidines 8.1B. Spirocyclic piperidines 8.1A and 8.1B can be used in place of 8.1 in Scheme 8 to afford the furanone coupled intermediates 8.4.

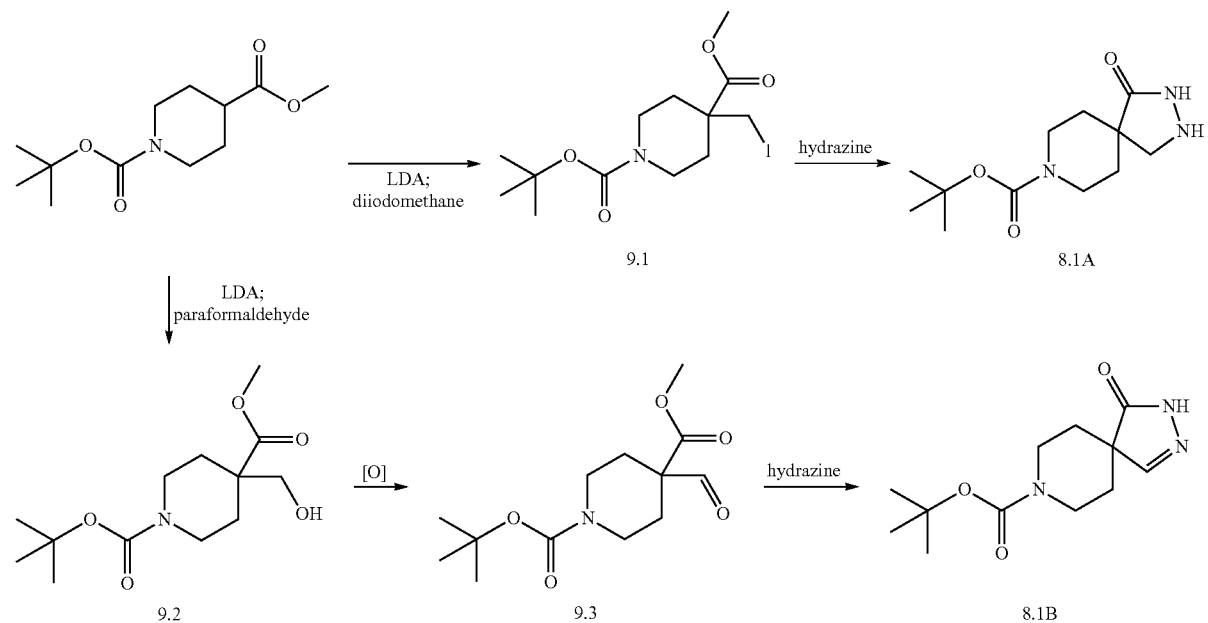

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate. Starting materials are commercially available or made by known procedures or as illustrated.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a WATERS ZQ platform with electrospray ionization in positive ion detection mode with an Agilent 1100 series HPLC with autosampler. The column was usually a WATERS XTERRA MS C18, 3.0×50 mm, 5 µm. The flow rate was 1 mL/min, and the injection volume was 10 µL. UV detection was in the range 210-400 nm. The mobile phase consisted of solvent A (water plus 0.05% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a WATERS Chromatography Workstation configured with an LC-MS System consisting of: WATERS ZQ single quad MS system with Electrospray Ionization, WATERS 2525 Gradient Pump, WATERS 2767 Injector/Collector, WATERS 996 PDA Detector, the MS Conditions of: 150-750 amu, Positive Electrospray, Collection Triggered by MS, and a WATERS SUNFIRE C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by BIOTAGE.

Concentration of solutions was carried out on a rotary evaporator under reduced pressure. Flash chromatography was usually performed using a BIOTAGE Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as the internal reference in CDCl$_3$ solutions, and residual CH$_3$OH peak or TMS was used as the internal reference in CD$_3$OD solutions. Coupling constants (J) were reported in hertz (Hz).

Chiral analytical chromatography was usually performed on one of CHIRALPAK AS, CHIRALPAK AD, CHIRALCEL OD, CHIRALCEL IA, or CHIRALCEL OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of CHIRALPAK AS, CHIRALPAK AD, CHIRALCEL OD, CHIRALCEL IA, or CHIRALCEL OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was conducted by supercritical fluid (SFC) conditions using one of CHIRALPAK AS, CHIRALPAK AD-H, CHIRALCEL OD-H, CHIRALPAK IC, or CHIRALCEL OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Flash chromatography was carried out on silica gel (230-400 mesh). NMR spectra were obtained in CDCl$_3$ solution unless otherwise noted. Coupling constants (J) are in hertz (Hz).

Abbreviations that may be used herein include: —C(O)CH$_3$ (Ac); —OC(O)CH$_3$ (OAc); ethyl acetate (EtOAc), benzyloxycarbonyl (Cbz); dibenzylideneacetone (dba); 11-chloroethylchloroformate (ACE-Cl); phenyl (Ph); dichloromethane (DCM), starting material (SM), diethyl ether (ether or Et$_2$O), trifluoroacetic acid (TFA), triethylamine (TEA), 1,8-Diazabicyclo[5.4.0]undec-7-ene (DBU); N,N-diisopropylethylamine (DIEA, Hunig's base, DIPEA), dimethylsulfide (DMS); 1-ethyl-3-(3-dimethylaminopropyl), carbodiimide (EDC, EDAC, or EDCI), 2-(7-Aza-1H-benzotriazole-1-yl)-1,1,3,3-tetramethyluronium hexafluorophosphate (HATU), 1-Hydroxybenzotriazole hydrate (HOBt), hexane (Hex); methyl tert-butyl ether (MTBE), Cyclopentyl methyl ether (CPME), 1,3-Bis(diphenylphosphino)propane (DPPP), 2-Dicyclohexylphosphino-2',4',6'-triisopropylbiphenyl (X-Phos), 1,2-dichloroethane (DCE), methanol (MeOH); N-bromo succinimide (NBS), N-chlorosuccinimide (NCS); N-iodosuccinimide (NIS), lithium diisopropylamide (LDA), tetrahydrofuran (THF), Diethylaminosulfur trifluoride (DAST); dimethylsulfoxide (DMSO), isopropanol (IPA), t-butyloxycarbonyl (Boc or BOC), di-t-butyl dicarbonate (BOC$_2$O, Boc$_2$O), acetic acid (AcOH; HOAc), N; N-dimethylformamide (DMF), 4-dimethylaminopyridine (DMAP), dimethylacetamide (DMA; DMAC); ethylene glycol tetraacetic acid (EGTA); 3-chloroperoxybenzoic acid (mCPBA); nicotinamide adenine dinucleotide phosphate (NADP), petroleum ether (PE), lithium aluminum hydride (LAH), di-isopropylamine (DIPA), Carbonyldiimidazole (CDI), p-toluenesulfonic acid (TsOH), p-toluene-SO$_2$— (tosyl or Ts), methane sulfonyl chloride or mesyl chloride (Ms-Cl), methanesulfonic acid (MsOH), CH$_3$SO$_2$-(mesyl or Ms), dimethoxyethane (DME), 1,1'-bis(diphenylphosphino)ferrocene (dppf, DPPF); Pd(dppf)Cl$_2$ or PdCl$_2$(dppf) is 1,1'-Bis(diphenylphosphino)ferrocene]dichloropalladium(II) which may be complexed with CH$_2$Cl$_2$, (Oxydi-2,1-phenylene)bis(diphenylphosphine) (DPEPhos); hexamethylphosphoramide (HMPA); isopropyl acetate (IPAc); N-methylmorpholine-N-oxide (NMO); tetrakis(triphenylphosphine)palladium (Pd(PPh$_3$)$_4$); tris(dibenzylidineacetone)dipalladium (Pd$_2$(dba)$_3$); Diethylaminodifluorosulfinium tetrafluoroborate (XtalFluor-E); 4,5-Bis(diphenylphosphino)-9,9-dimethylxanthene (Xantphos); N,N,N',N'-Tetramethylethylenediamine (TMEDA); [1,4-Bis (diphenylphosphino)butane](1,5-cyclooctadiene)rhodium(I) tetrafluoroborate (Rh(COD)BF$_4$); round-bottom flask (RB or RBF); aqueous (aq); saturated aqueous (sat'd), saturated aqueous sodium chloride solution (brine); medium pressure liquid chromatography (MPLC), high pressure liquid chromatography (HPLC), flash chromatography (FC); liquid chromatography (LC), supercritical fluid chromatography (SFC); thin layer chromatography (TLC), mass spectrum (ms or MS); liquid chromatography-mass spectrometry (LC-MS or LC/MS), column volume (CV), room temperature (rt, r.t. or RT), hour(s) (h or hr), minute(s) (min), retention time (R$_t$); gram(s) (g); milligram(s) (mg); milliliter(s) (mL); microliter(s) (μL); millimole (mmol). CELITE is a trademark name for diatomaceous earth, and SOLKA FLOK is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate. Any Intermediates described below may be referred to herein by their number preceded by "I-" or "Int-." For illustration, in the example titled "Intermediate 3," the racemic parent title compound would be referred to as Intermediate 3 (or I-3), and the separated stereoisomers are noted as Intermediates 3A and 3B (or I-3A and I-3B). In some examples, compounds having a chiral center were derived synthetically from a single isomer intermediate; e.g., Example 4A was made using stereoisomer I-9A. Except for a defined chiral center in a parent isomer mixture, absolute stereochemistry (R or S) of each of the separated isomers was not determined, unless specifically described otherwise. An asterisk (*) may be used in a chemical structure drawing that indicates the location of a chiral center.

INTERMEDIATE 1

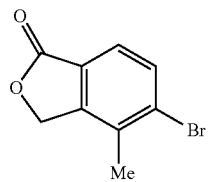

5-bromo-4-methyl-2-benzofuran-1(3H)-one

Step A: (3-bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. $^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a CELITE pad, washed with EtOAc, adsorbed onto silica and purified by silica gel chromatography to afford the title compound. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

INTERMEDIATE 2

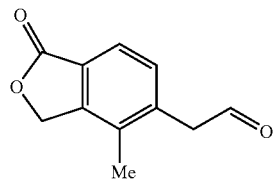

(4-Methyl-1-oxo-1,3-dihydro-2-benzofuran-5-yl) acetaldehyde

Step A: 4-Methyl-5-prop-2-en-1-yl-2-benzofuran-1 (3H)-one

To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh$_3$)$_4$(244 mg, 0.211 mmol), lithium chloride (179 mg, 4.23 mmol), and toluene (15 mL). The reaction was purged with nitrogen 2 times and was then heated at reflux for 4 hours. The product was separated by silica gel chromatography to give 4-methyl-5-prop-2-en-1-yl-2-benzofuran-1(3H)-one.

Step B: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford the title compound. $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

INTERMEDIATE 3

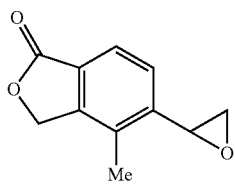

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$ Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g REDI-SEP column and 0-80% ETOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g REDI-SEP column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H). LC-MS: M+1=191.

INTERMEDIATES 3A AND 3B (Method 1)

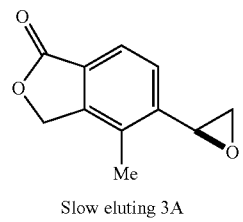

Slow eluting 3A

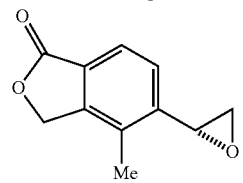

Fast eluting 3B

3A: 4-methyl-5-[(2S)-oxiran-2-yl]-2-benzofuran-1(3H)-one

3B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 µl Injections were spaced every 2.12 mins. The fast epoxide (4-methyl-5-[(2R)-oxiran-2-yl]-2-benzofuran-1(3H)-one, 3B) eluted first, and the slow epoxide (4-methyl-5-[(2S)-oxiran-2-yl]-2-benzofuran-1(3H)-one, 3A) eluted second.

Alternatively, the resolution could also be achieved using a mobile phase of 8% MeOH/92% CO$_2$ with a flow rate of 100 mL/min. In that case the sample was prepared by dissolving in methanol, 20 mg/mL, and using a 1 mL volume per injection. After separation, the fractions were dried via rotary evaporator at bath temperature 40° C.

The absolute stereochemistry of each enantiomer was inferred based on the X-ray crystal structure determination of a final compound made with 3B and by Mosher ester and Trost ester $^H$NMR analysis of esters made starting from 3B. Both epoxide isomers find utility in the present invention.

INTERMEDIATE 3B (Method 2)

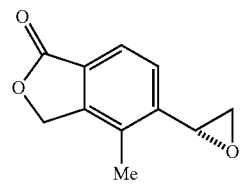

4-methyl-5-[(2R)-oxiran-2-yl]-2-benzofuran-1(3H)-one

Step A: 3-hydroxymethyl-2-methyl phenol

To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which $BF_3$—$OEt_2$ (321 mL, 2.53 mol) was added slowly over 1.5 hours. The slurry was aged at 10° C.–15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min. The organic solvents were then removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol. $^1$H-NMR (400 MHz, DMSO-$d_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane:MTBE (500 mL), followed by heptane (500 mL). The solid was dried under vacuum, providing 4-bromo-3-hydroxymethyl-2-methyl phenol. $^1$H NMR (400 MHz, DMSO-$d_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C:
5-Hydroxy-4-methyl-3H-isobenzofuran-1-one

To a 2 L 3 neck flask equipped with overhead stirrer, $N_2$ inlet, and condenser were charged 4-bromo-3-hydroxymethyl-2-methyl phenol (100 g, 461 mmol), CuCN (83.0 g, 921 mmol), and DMF (500 mL). The solution was sparged with $N_2$ for 15 min then heated to 145° C. to obtain a homogeneous solution. The solution was aged at 145° C. for 2 h, and the reaction mixture was then cooled to 95° C. 41.5 mL water was added (sparged with $N_2$), and the reaction aged for 20 h. The reaction was cooled to RT then the solids filtered through SOLKA FLOK and the cake washed with 50 mL DMF. To a 3 L flask containing 1 L EtOAc was added the DMF filtrate. A precipitate coating formed in bottom of flask. The DMF/EtOAc suspension was filtered through SOLKA FLOK and the cake was washed with 250 mL EtOAc. The resulting filtrate was washed with 5% brine solution (3×500 mL). The aqueous layers were extracted with 500 mL EtOAc and the combined organics were dried over MgSO4, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one. $^1$H NMR (400 MHz, DMSO-$d_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D:
4-methyl-1-oxo-1,3-dihydroisobenzofuran-5-yl trifluoromethanesulfonate

5-Hydroxy-4-methyl-3H-isobenzofuran-1-one (46.8 g, 285 mmol) was suspended in dichloromethane (935 mL) in a 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), and then stirred with DARCO® KB (activated carbon, 25 g) for 15 min. The biphasic mixture was filtered over SOLKA FLOK, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, and the solid was washed with heptane and dried under vacuum and nitrogen, providing trifluoromethanesulfonic acid 4-methyl-1-oxo-1,3-dihydro-isobenzofuran-5-yl ester. $^1$H NMR (400 MHz, $CDCl_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol) and then $Et_3N$ (35.6 mL, 255 mmol). The solution was sparged with $N_2$ for 20 min. To the solution was added $Pd(OAc)_2$ (1.19 g, 5.32 mmol) and DPPP (2.41 g, 5.85 mmol) and sparged for an additional 10 min then heated to 80° C. After a 1 hr age, the solution was cooled to <10° C. and then quenched with 630 mL EtOAc and washed with 5% $NH_4Cl$ (2×315 mL) and 10% brine (2×315 mL). The resultant was then dried over $MgSO_4$, filtered, concentrated by rotary evaporation, and flushed with EtOAc (3×100 mL) to remove excess butyl vinyl ether. Crude 5-(1-butoxy-vinyl)-

4-methyl-3H-isobenzofuran-1-one resulted. $^1$H NMR (400 MHz, DMSO-d$_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one. $^1$H NMR (400 MHz, DMSO-d$_6$): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzofuran-1(3H)-one 5-(2-Bromo-acetyl)-4-methyl-3H-isobenzofuran-1-one (48.8 g, 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT and the aqueous layer was extracted with 1.22 L isopropyl acetate (IPAc). The aqueous layer was re-extracted with 400 mL IPAc and the combined organics were washed with 400 mL 20% brine solution, and then dried over MgSO$_4$, and filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The crystalline solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

INTERMEDIATE 4

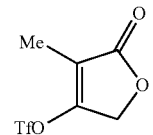

4-methyl-5-oxo-2,5-dihydrofuran-3-yl trifluoromethanesulfonate

Step A: ethyl 4-bromo-2-methyl-3-oxobutanoate

To a solution of ethyl 2-methyl-3-oxobutanoate (5.05 g, 35.0 mmol) in water (10 mL) at 0° C. was added bromine (1.805 mL, 35.0 mmol) dropwise over 2 h. The resulting solution was stirred at rt for 16 h. The reaction mixture was extracted with ethyl acetate. The organic phase was dried over sodium sulfate, and concentrated to give ethyl 4-bromo-2-methyl-3-oxobutanoate. $^1$HNMR (500 MHz, CDCl$_3$), δ4.322-4.274 (m, 2H), 2.455 (s, 2H), 1.991 (s, 3H), 1.337-1.309 (t, 3H).

Step B: 4-hydroxy-3-methylfuran-2(5H)-one

Ethyl 4-bromo-2-methyl-3-oxobutanoate (7.81 g, 35 mmol) was treated with hydrogen bromide (0.040 mL, 48%, 0.35 mmol) and the mixture was heated at 100° C. for 6 h. The precipitate was collected by filtration followed by washing with ethyl acetate to give 4-hydroxy-3-methylfuran-2(5H)-one. $^1$HNMR (500 MHz, CDCl$_3$), δ4.595 (s, 2H), 3.314 (s, 1H), 1.668 (s, 3H).

Step C: 4-methyl-5-oxo-2,5-dihydrofuran-3-yl trifluoromethanesulfonate

To the solution of 4-hydroxy-3-methylfuran-2(5H)-one (400 mg, 3.51 mmol) in dichloromethane (10 mL) at −78° C. was added 2,6-lutidine (0.612 mL, 5.26 mmol) and triflic anhydride (0.711 mL, 4.21 mmol) dropwise. The reaction temperature was maintained at −78° C. for 0.5 h before being warmed to rt for 1 h. The mixture was diluted with DCM (100 mL) and washed with 1 N hydrogen chloride (3 times 100 mL), then with diluted sodium bicarbonate solution, then dried over sodium sulfate, and concentrated to give 4-methyl-5-oxo-2,5-dihydrofuran-3-yl trifluoromethanesulfonate. LC/MS: (M+1)$^+$: 247.0.

INTERMEDIATE 5

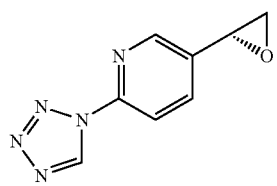

5A

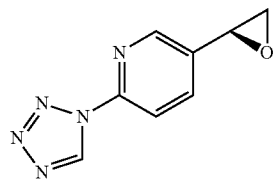

5B (R)-5-(Oxiran-2-yl)-2-(1H-tetrazol-1-yl)pyridine (5A) and (S)-5-(Oxiran-2-yl)-2-(1H-tetrazol-1-yl)pyridine (5B)

Step A: 5-Bromo-2-(1H-tetrazol-1-yl)pyridine

To a solution of 5-bromopyridin-2-amine (5.0 g, 28.9 mmol) in acetic acid (40 mL, 699 mmol) was added (diethoxymethoxy) ethane (7.70 mL, 46.2 mmol), followed by sodium azide (2.82 g, 43.3 mmol). The mixture was heated at 80° C. for 1 h, cooled to room temperature and diluted with water. Precipitate was collected by filtration and dried under high vacuum to provide the title compound.

Step B: 5-Ethenyl-2-(1H-tetrazol-1-yl)pyridine

To a stirring solution of 5-bromo-2-(1H-tetrazol-1-yl)pyridine (1.0 g, 4.42 mmol) in EtOH (70 mL) was added bis[(diphenylphosphino)ferrocene]dichloropalladium(II) complex with dichloromethane (0.361 g, 0.442 mmol), potassium vinyl trifluoroborate (1.18 g, 8.85 mmol, 2 equiv.), triethylamine (1.23 mL, 8.85 mmol, 2 equiv), and water (0.5 mL). The reaction mixture was heated at reflux (90° C., oil bath) under $N_2$. Upon completion (1-2 h) as determined by reverse phase HPLC-MS and TLC (eluent: 10% ethyl acetate in hexane), the mixture was cooled to room temperature, and then diluted with water. The organic layer was separated, and the aqueous layer was extracted with EtOAc. The combined organic layers were washed with brine, dried over $MgSO_4$, and concentrated. The crude material was chromatographed over a column of $SiO_2$ (0-20% EtOAc in hexane as eluent). Evaporation of the solvent yielded the title compound. LCMS $[M+1]^+=174.0$.

Step C: 5-(Oxiran-2-yl)-2-(1H-tetrazol-1-yl)pyridine (5)

To a solution of 5-ethenyl-2-(1H-tetrazol-1-yl)pyridine (0.664 g, 3.83 mmol) in a 2:1 ratio of $H_2O$:t-BuOH (30 mL) was added N-bromosuccinimide (0.751 g, 4.22 mmol) in portions over 5 min. The mixture was heated at 40° C. for 1 h, cooled to 5° C., made basic with sodium hydroxide aqueous solution (0.46 g in 5 mL of $H_2O$, 11.50 mmol), stirred for another 1 h at the same temperature, and poured into $H_2O$ (10 mL). The product precipitated out. The solid was collected by filtration, washed with water, and dried in vacuo. $^1H$ NMR (500 MHz, DMSO-$d_6$), δ 10.17 (s, 1H), 8.60 (d, J=1.4 Hz, 1H), 8.04-7.99 (m, 2H), 4.14 (dd, J=2.7 Hz, J=2.8 Hz, 1H), 3.23 (t, J=4.6 Hz, 1H), 3.02 (dd, J=25 Hz, 1H); LCMS $[M+1]^+=190$. Further chiral separation (CHIRALPAK AD-H 30×250 mm, 50% MeOH/$CO_2$, 70 mL/min, 100 bar, 46 mg in MeOH/DCM) afforded faster eluted 5A (R)-5-(oxiran-2-yl)-2-1H-tetrazol-1-yl)pyridine and slower eluted 5B (S)-5-(oxiran-2-yl)-2-(1H-tetrazol-1-yl)pyridine. Absolute chemistry was determined by using Vibrational Circular Dichroism (VCD) spectroscopy with high confidence. Analysis was done comparing experimental data to the calculated VCD and IR spectra of the (R) and (S) compounds.

INTERMEDIATES 6A and 6B

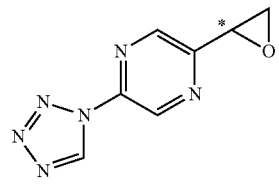

Faster eluting enantiomer

6A

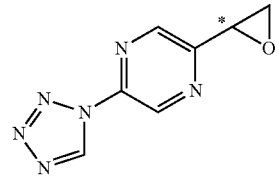

Slower eluting enantiomer

6B (R)-2-(Oxiran-2-yl)-5-(1H-tetrazol-1-yl)pyrazine and (S)-2-(Oxiran-2-yl)-5-(1H-tetrazol-1-yl)pyrazine Step A: 2-Bromo-5-(1H-tetrazol-1-yl)pyrazine To a solution of 5-bromopyrazin-2-amine (10.75 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred for another five min, and this was followed by addition of azidotrimethylsilane (12.09 ml, 92 mmol). Stirring continued at rt for 2 days, and the mixture was concentrated under reduced pressure. Recrystallization of the residue from ethyl acetate afforded 2-bromo-5-(1H-tetrazol-1-yl)pyrazine. LCMS $[M+2+1]^+=228.9$.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.22 g, 99.0 mmol), 1,1'-bis(diphenylphosphino)ferrocene-palladium(ii) dichloride dichloromethane complex (2.01 g, 2.47 mmol), and TEA (13.75 ml, 99.0 mmol) in ethanol (150 ml) was heated at reflux at 82° C. for 4 h. The reaction mixture was cooled to rt, and the precipitate was filtered off. The filtrate was concentrated, and the residue was purified by flash chromatography (Biotage, Si, ethyl acetate in hexane: 35 to 45%) affording 2-(1H-tetrazol-1-yl)-5-vinylpyrazine LCMS $[M+1]^+=175.10$. The filter cake was stirred in DCM (50 mL), and the solid was filtered off. The filtrate was concentrated to afford more 2-(1H-tetrazol-1-yl)-5-vinylpyrazine.

Step C: 2-(Oxiran-2-yl)-5-(1H-tetrazol-1-yl)pyrazine

To a suspension of 2-(1H-tetrazol-1-yl)-5-vinylpyrazine (6.7 g, 38.5 mmol) in t-BuOH:water (96 ml: 190 ml) was added N-bromosuccinimide (7.53 g, 42.3 mmol) in portions at rt. The mixture was heated at 50° C. for 1 h, and cooled to 0° C. in an ice bath. NaOH (4.61 g in 30 mL water, 115 mmol) was added dropwise, and the resulting mixture was stirred at the same temperature for 20 min. The product was collected by filtration, washed with water, and dried under vacuum to give 2-(1H-tetrazol-1-yl)-5-vinylpyrazine LCMS [M+1]⁺=191.07. Chiral separation (CHIRALPAK AD-H 30×250 mm, 50% MeOH/CO₂, 70 mL/min, 100 bar, MeOH/DCM) afforded faster eluted isomer 6A and slower eluted isomer 6B. LCMS [M+1]⁺=191.1. Both isomers were useful for the preparation of potent ROMK inhibitors.

The following epoxide intermediates in Table 1 were prepared employing a similar synthetic method as that described for Intermediates 5, 5A, 5B or 6, 6A, 6B. Column 2 shows the structure of the starting material followed by the method used (either I-5 for the procedure described for Intermediate 5, or I-6 for the procedure described for Intermediate 6). Note that the absolute stereochemistry was not determined unambiguously for these intermediates. Both isomers were useful for the preparation of potent ROMK inhibitors.

TABLE 1

Epoxides prepared using the method described for 1-5 or 1-6

| Intermediate No. | Column 2 | Structure and name | Structure and name | LC-MS [M + 1]⁺ |
|---|---|---|---|---|
| 7 | 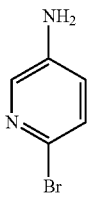<br>Method: I-5 | 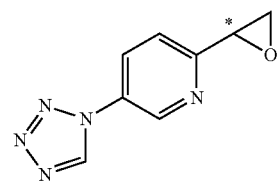 [SMILES: c1cc(C2CO2)ncc1-n1cnnn1]<br>Fast eluted 7A | 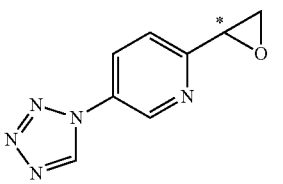 [SMILES: c1cc(C2CO2)ncc1-n1cnnn1]<br>Slow eluted 7B | 190.10 |
| 8 | 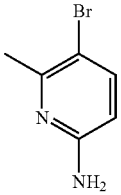<br>Method: I-5 | 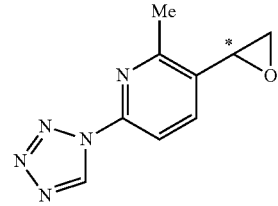 [SMILES: Cc1nc(-n2cnnn2)ccc1C1CO1]<br>Fast eluted 8A | 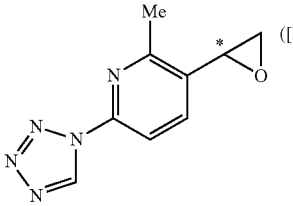<br>Slow eluted 8B | 188.10 ([M + 1 − 28]⁺) |
| 9 | 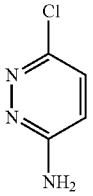<br>Method: I-6 | 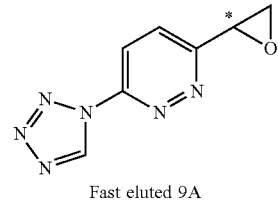<br>Fast eluted 9A | 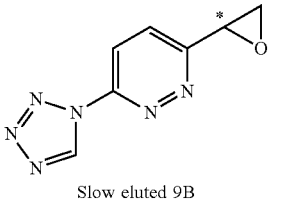<br>Slow eluted 9B | 191.16 |
| 10 | 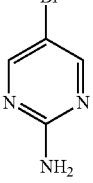<br>Method: I-6 | 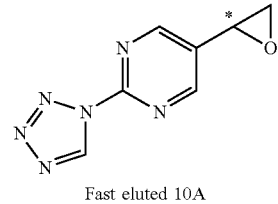<br>Fast eluted 10A<br>Chiralpak IA column | 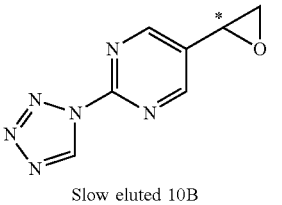<br>Slow eluted 10B | 191.07 |
| 11 | 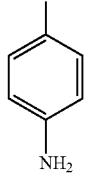<br>Method: I-6 | 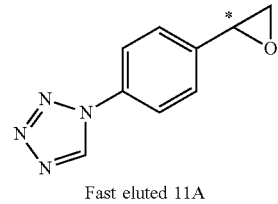<br>Fast eluted 11A | 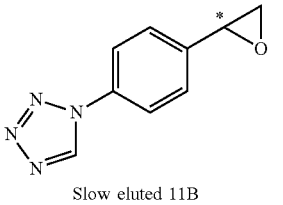<br>Slow eluted 11B | 189.13 |

TABLE 1-continued

Epoxides prepared using the method described for 1-5 or 1-6

| Intermediate No. | Column 2 | Structure and name | Structure and name | LC-MS [M + 1]+ |
|---|---|---|---|---|
| 12 | Br / Me / NH2 ; Method: I-6 | Fast eluted 12A | Slow eluted 12B | 203.1 |
| 13 | Br / OCH3 / NH2 ; Method: I-6 | Fast eluted 13A | Slow eluted 13B | 219.3 |
| 14 | Br / F / NH2 ; Method: I-6 | Fast eluted 14A | Slow eluted 14B | 207.3 |

INTERMEDIATE 15

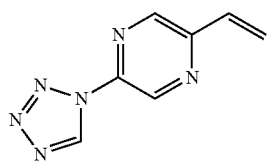

2-(1H-Tetrazol-1-yl)-5-vinylpyrazine

Step A: 2-Bromo-5-(1H-tetrazol-1-yl)pyrazine

To a solution of 5-bromopyrazin-2-amine (10.75 g, 57.5 mmol) in ethyl acetate (150 mL) was added trimethylsilyl 2,2,2-trifluoroacetate (17 mL, 98 mmol). The mixture was stirred for 5 min, and triethoxymethane (17.21 ml, 103 mmol) was added. After the resulting mixture was stirred for another five min, azidotrimethylsilane (12.09 ml, 92 mmol) was added. Stirring continued at rt for 2 days, and the mixture was concentrated under reduced pressure. Recrystallization of the residue from ethyl acetate afforded the title compound. LCMS [M+2+1]+=228.9.

Step B: 2-(1H-Tetrazol-1-yl)-5-vinylpyrazine

A solution of 2-bromo-5-(1H-tetrazol-1-yl)pyrazine (11.2 g, 49.3 mmol), potassium vinyltrifluoroborate (13.2 g, 99.0 mmol), 1,1'-bis(diphenylphosphino)ferrocene-palladium(ii) dichloride dichloromethane complex (2.01 g, 2.47 mmol), and TEA (13.8 mL, 99.0 mmol) in ethanol (150 mL) was heated at reflux at 82° C. for 4 h. The reaction mixture was allowed to cool to rt, and the precipitation was filtered off. The filtrate was concentrated, and the residue was purified by flash chromatography (Biotage, Si, ethyl acetate in hexane: 35 to 45%) affording the title compound. The filter cake was stirred in DCM (50 mL), and the solid was filtered off. The filtrate was concentrated to afford more of the title compound. LCMS [M+1]+=175.1.

The following arylvinyl intermediate in Table 2 was prepared employing a similar synthetic method as that described for Intermediate 15 using the noted starting material.

TABLE 2

Arylvinyl prepared according to the method described for INTERMEDIATE 15

| Intermediate No. | Starting material | Structure and name | LC-MS [M + 1]+ |
|---|---|---|---|
| 16 | Br / N=N / NH2 | 3-(1H-tetrazol-1-yl)-6-vinylpyridazine | 175 |

INTERMEDIATE 17

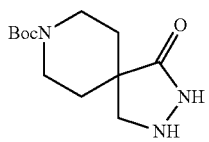

tert-butyl
1-oxo-2,3,8-triazaspiro[4.5]decane-8-carboxylate

Step A: 1-tert-butyl 4-methyl 4-(iodomethyl)piperidine-1,4-dicarboxylate

A solution of 1-tert-butyl 4-methyl piperidine-1,4-dicarboxylate (5.00 g, 20.6 mmol) in THF (70 mL) was added dropwise to a solution of LDA (2 M in THF, 15 mL, 30 mmol) at −78° C. After being stirred for 1 h, a solution of diiodomethane (8.24 g, 30.9 mmol) in THF (20 mL) was added slowly at −78° C. The reaction was stirred at −78° C. for 4 h and allowed to warm to room temperature. After 18 h, the reaction mixture was quenched with saturated aqueous ammonia chloride solution. The solvent was removed in vacuo and the aqueous layer was extracted with ethyl acetate. The combined organic layer was washed with brine, dried over anhydrous sodium sulfate, filtered and concentrated. The resulting residue was purified by flash chromatography (0-30% ethyl acetate in petroleum ether) to give the title compound. LC-MS (ESI, m/z): 384 [M+1]+.

Step B: tert-butyl 1-oxo-2,3,8-triazaspiro[4.5]decane-8-carboxylate

A mixture of 1-tert-butyl 4-methyl 4-(iodomethyl)piperidine-1,4-dicarboxylate (4.50 g, 0.012 mol) in anhydrous hydrazine (10 mL) was heated at 140° C. for 3 h. After being cooled to room temperature, the mixture was diluted with tert-butylmethyl ether and filtered to afford the title compound. 1H-NMR (400 MHz, DMSO) δ ppm 3.75-3.78 (m, 2H), 3.10 (s, 2H), 2.83-2.85 (m, 2H), 1.44-1.48 (m, 4H), 1.39 (s, 9H). LC-MS (ESI, m/z): 256 [M+1]+.

INTERMEDIATE 18

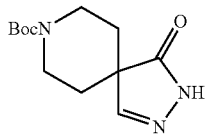

tert-butyl 4-oxo-2,3,8-triazaspiro[4.5]dec-1-ene-8-carboxylate

Step A: 1-tert-butyl 4-methyl 4-(hydroxymethyl)piperidine-1,4-dicarboxylate

To a mixture of 1-tert-butyl 4-methyl piperidine-1,4-dicarboxylate (5.00 g, 20.6 mmol) in THF (100 mL) was added lithium diisopropylamide (2 M in THF, 15 mL, 30 mmol) dropwise at −78° C. under nitrogen atmosphere. After the addition, the mixture was stirred at −78° C. for 1 h, and paraformaldehyde (2.78 g, 30.9 mmol) was then added. After stirring at −78° C. for 2 h, the mixture was allowed to warm to room temperature and then it was stirred for 15 h. The mixture was quenched with saturated aqueous ammonia chloride solution. The organic layer was separated and the aqueous layer was extracted with ethyl acetate three times. The combined organic layer was dried over anhydrous sodium sulfate, filtered and concentrated. The resulting residue was purified by flash chromatography (0-30% ethyl acetate in petroleum ether) to give the title compound. LC-MS (ESI, m/z): 274 [M+1]+.

Step B: 1-tert-butyl 4-methyl 4-formylpiperidine-1,4-dicarboxylate

To a solution of oxalyl dichloride (1.02 g, 8.0 mmol) in dry dichloromethane (50 mL) was added dimethyl sulfoxide (1.25 g, 16.0 mmol) at −78° C. under nitrogen atmosphere. After the mixture was stirred at −78° C. for 30 min, 1-tert-butyl 4-methyl 4-(hydroxymethyl)piperidine-1,4-dicarboxylate (1.09 g, 4.0 mmol) was added. After stirring at −78° C. for another 1 h, the reaction mixture was allowed to warm to −40° C. and triethylamine (4.0 mL, 32.0 mmol) was added thereto. The mixture was stirred at −40° C. for 1 h. The mixture was diluted with dichloromethane, washed with water and brine, dried over anhydrous magnesium sulfate and filtered. The filtrate was concentrated to give the title compound. LC-MS (ESI, m/z): 272 [M+1]+.

Step C: tert-butyl 4-oxo-2,3,8-triazaspiro[4.5]dec-1-ene-8-carboxylate

To a solution of 1-tert-butyl 4-methyl 4-formylpiperidine-1,4-dicarboxylate (1.00 g, 4.15 mmol) in methanol (10 mL) was added hydrazine monohydrate (622 mg, 12.45 mmol), and the mixture was stirred at room temperature for 16 h. The solvent was removed by evaporation and the residue was purified by flash chromatography (0-20% ethyl acetate in petroleum ether) to give the title compound. 1H-NMR (400 MHz, CDCl3) δ ppm 9.08 (s, 1H), 7.32 (s, 1H), 3.95-3.92 (m, 2H), 3.27-3.20 (m, 2H), 1.74-1.70 (m, 2H), 1.59-1.56 (m, 2H), 1.38 (s, 9H). LC-MS (ESI, m/z): 254 [M+1]+.

INTERMEDIATE 19

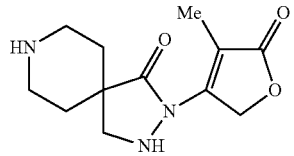

2-(4-methyl-5-oxo-2,5-dihydrofuran-3-yl)-2,3,8-triazaspiro[4.5]decan-1-one

Step A: tert-butyl 2-(4-methyl-5-oxo-2,5-dihydrofuran-3-yl)-1-oxo-2,3,8-triazaspiro[4.5]decane-8-carboxylate A 100-mL round bottom flask was charged with tert-butyl 1-oxo-2,3,8-triazaspiro[4.5]decane-8-carboxylate (Int. 17, 450 mg, 1.76 mmol), cesium carbonate (1.7 g, 5.3 mmol), tris(dibenzylideneacetone)dipalladium (80 mg, 0.088 mmol) and Xantphos (102 mg, 0.176 mmol). The flask was degassed and purged with nitrogen, then dioxane (50 mL) and 4-methyl-5-oxo-2,5-dihydrofuran-3-yltrifluoromethanesulfonate (651 mg, 2.65 mmol) was added under nitrogen atmosphere. The flask was degassed and refilled with nitrogen several times. The reaction mixture was stirred at 100° C. for 7 h. The solid was filtered off and the filtrate was concentrated and purified by flash chromatography (0-30% ethyl acetate in petroleum ether) to give the title compound. $^1$H NMR (400 MHz, CDCl$_3$) δ 5.07 (s, 2H), 3.87 (d, J=12.8 Hz, 2H), 3.34 (s, 2H), 3.02 (t, J=11.2 Hz, 2H), 2.00 (s, 3H), 1.80-1.76 (m, 2H), 1.54-1.51 (m, 2H), 1.30 (s, 9H). LC-MS (m/z): 352 [M+H]$^+$.

Step B: 2-(4-methyl-5-oxo-2,5-dihydrofuran-3-yl)-2,3,8-triazaspiro[4.5]decan-1-one A mixture of tert-butyl 2-(4-methyl-5-oxo-2,5-dihydrofuran-3-yl)-1-oxo-2,3,8-triazaspiro[4.5]decane-8-carboxylate (100 mg, 0.28 mmol) in a mixed solvent of trifluoroacetic acid (2 mL) and dichloromethane (2 mL) was stirred at room temperature for 2 h. After the starting material was consumed completely monitored by LCMS, the mixture was concentrated to give the title compound, which was used for the next step without further purification. LC-MS (m/z): 252 [M+H]$^+$.

INTERMEDIATE 20

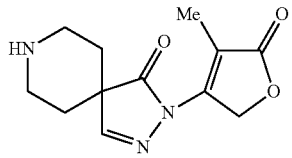

2-(4-methyl-5-oxo-2,5-dihydrofuran-3-yl)-2,3,8-triazaspiro[4.5]dec-3-en-1-one

Step A: tert-butyl 3-(4-methyl-5-oxo-2,5-dihydrofuran-3-yl)-4-oxo-2,3,8-triazaspiro[4.5]dec-1-ene-8-carboxylate A 100-mL round bottom flask was charged with tert-butyl 4-oxo-2,3,8-triazaspiro[4.5]dec-1-ene-8-carboxylate (Int. 18, 600 mg, 1.76 mmol), cesium carbonate (1.2 g, 3.56 mmol), tris(dibenzylideneacetone)dipalladium (54 mg, 0.060 mmol) and Xantphos (103 mg, 0.18 mmol). The flask was degassed and purged with nitrogen, then dioxane (50 mL) and 4-methyl-5-oxo-2,5-dihydrofuran-3-yltrifluoromethanesulfonate (641 mg, 2.61 mmol) was added under nitrogen atmosphere. The flask was degassed and refilled with nitrogen several times. The mixture was stirred at 90° C. for 17 h. The solid was filtered off and the filtrate was concentrated and purified by flash chromatography (0-25% ethyl acetate in petroleum ether) to afford the title compound. $^1$H NMR (400 MHz, CDCl$_3$) δ 7.62 (s, 1H), 5.17 (d, J=1.6 Hz, 2H), 3.95-3.92 (m, 2H), 3.40-3.33 (m, 2H), 2.09 (s, 3H), 1.84-1.71 (m, 4H), 1.43 (s, 9H). LC-MS (m/z): 350 [M+H]$^+$.

Step B: 2-(4-methyl-5-oxo-2,5-dihydrofuran-3-yl)-2,3,8-triazaspiro[4.5]dec-3-en-1-one A mixture of tert-butyl 3-(4-methyl-5-oxo-2,5-dihydrofuran-3-yl)-4-oxo-2,3,8-triazaspiro[4.5]dec-1-ene-8-carboxylate (60 mg, 0.17 mmol) in a mixed solvent of trifluoroacetic acid (1 mL) and dichloromethane (1 mL) was stirred at room temperature for 2 h. After the starting material was consumed completely monitored by LCMS, the mixture was concentrated to give the desired product (43 mg, 100%) as brown oil, which was used for the next step without further purification. LC-MS (m/z): 250 [M+H]$^+$.

Example 1

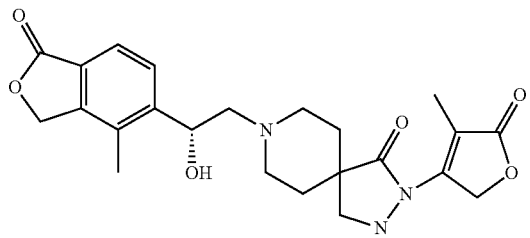 [SMILES: CC1=C(N2NCC3(CCN(C[C@H](O)c4ccc5c(c4C)COC5=O)CC3)C2=O)COC1=O]

(R)-8-(2-hydroxy-2-(4-methyl-1-oxo-1,3-dihydroisobenzofuran-5-yl)ethyl)-2-(4-methyl-5-oxo-2,5-dihydrofuran-3-yl)-2,3,8-triazaspiro[4.5]decan-1-one To a solution of 2-(4-methyl-5-oxo-2,5-dihydrofuran-3-yl)-2,3,8-triazaspiro[4.5]decan-1-one (Int. 19, 60 mg, 0.16 mmol) and triethylamine (48 mg, 0.48 mmol) in ethanol (4 mL) was added (R)-4-methyl-5-(oxiran-2-yl)isobenzofuran-1(3H)-one (31 mg, 0.16 mmol), and the mixture was stirred at 90° C. for 18 h. The mixture was cooled to room temperature and then concentrated to give the crude product, which was purified by preparative TLC (dichloromethane:methanol=10:1) to afford the title compound. $^1$H NMR (400 MHz, MeOD) δ 7.69 (d, J=8.0 Hz, 1H), 7.62 (d, J=8.0 Hz, 1H), 5.27 (s, 2H), 5.22-5.19 (m, 1H), 5.08 (d, J=1.6 Hz, 2H), 3.20 (s, 2H), 3.11-3.04 (m, 2H), 2.69-2.45 (m, 4H), 2.26 (s, 3H), 1.95 (s, 3H), 1.91-1.70 (m, 4H). LC-MS (m/z): 442 [M+H]$^+$.

The Examples in the table below were prepared in an analogous fashion as that described for (R)-8-(2-hydroxy-2-(4-methyl-1-oxo-1,3-dihydroisobenzofuran-5-yl)ethyl)-2-(4-methyl-5-oxo-2,5-dihydrofuran-3-yl)-2,3,8-triazaspiro[4.5]decan-1-one from the amine and epoxide Intermediates indicated, which were all prepared as described above.

TABLE 3

| # | Intermediates | Structure | LC-MS M+1 | IUPAC name |
|---|---|---|---|---|
| 2A | 5A, 19 | 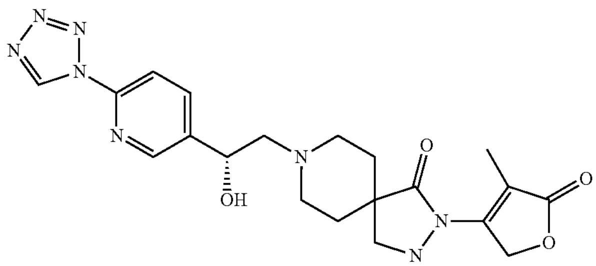 [SMILES: CC1=C(N2NCC3(CCN(C[C@H](O)c4ccc(-n5cnnn5)nc4)CC3)C2=O)COC1=O] | 441 | (R)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one |
| 2B | 5B, 19 | 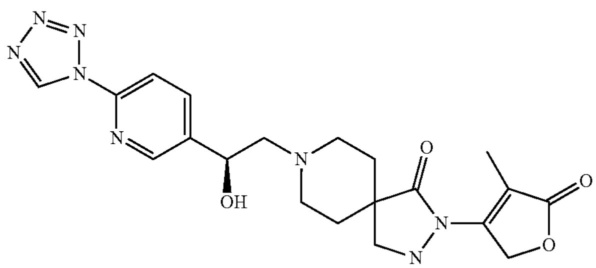 [SMILES: CC1=C(N2NCC3(CCN(C[C@@H](O)c4ccc(-n5cnnn5)nc4)CC3)C2=O)COC1=O] | 441 | (S)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one |
| 3A | 5A, 20 | 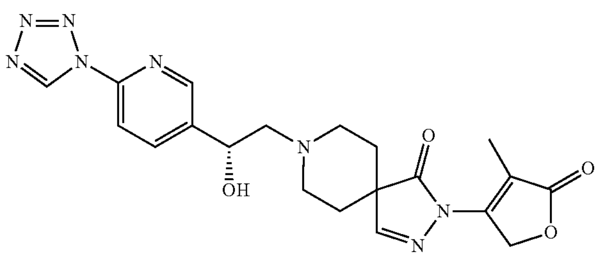 [SMILES: CC1=C(N2N=CC3(CCN(C[C@H](O)c4ccc(-n5cnnn5)nc4)CC3)C2=O)COC1=O] | 439 | (R)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one |
| 3B | 5B, 20 | 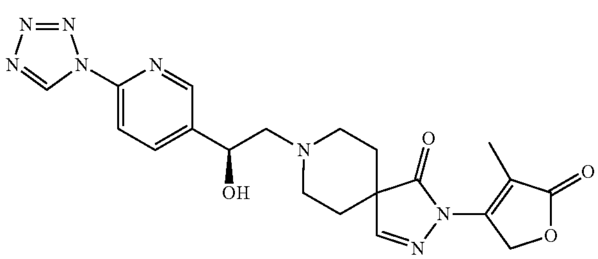 [SMILES: CC1=C(N2N=CC3(CCN(C[C@@H](O)c4ccc(-n5cnnn5)nc4)CC3)C2=O)COC1=O] | 439 | (S)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one |
| 4A | 9A, 20 | 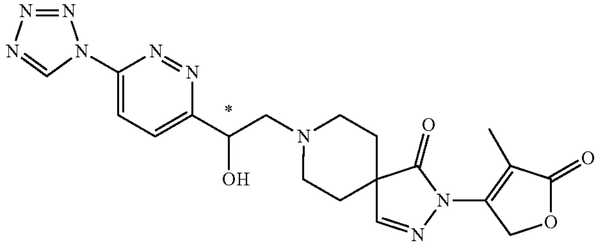 | 440 | 8-(2-(6-(1H-tetrazol-1-yl)pyridazin-3-yl)-2-hydroxyethyl)-2-(4-methyl-5-oxo-2,5-dihydrofuran-3-yl)-2,3,8-triazaspiro[4.5]dec-3-en-1-one (single enantiomer, absolute stereochemistry not established) |

Example 5

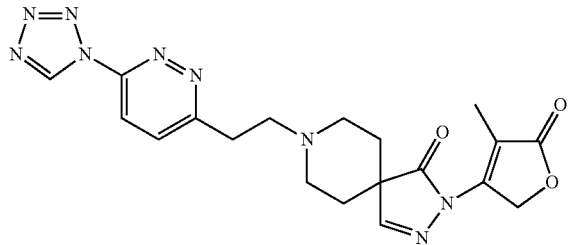 [SMILES: CC1=C(N2N=CC3(CCN(CCc4ccc(-n5cnnn5)nn4)CC3)C2=O)COC1=O]

8-(2-(6-(1H-tetrazol-1-yl)pyridazin-3-yl)ethyl)-2-(4-methyl-5-oxo-2,5-dihydrofuran-3-yl)-2,3,8-triazaspiro[4.5]dec-3-en-1-one A mixture of 3-(1H-tetrazol-1-yl)-6-vinylpyridazine (Int. 16, 50 mg, 0.29 mmol), 2-(4-methyl-5-oxo-2,5-dihydrofuran-3-yl)-2,3,8-triazaspiro[4.5]dec-3-en-1-one (Int. 20, 24 mg, 0.097 mmol), DPEphos (5.4 mg, 0.0097 mmol) and Rh(COD)BF$_4$ (3.9 mg, 0.0097 mmol) in toluene (1.5 mL) was stirred at 80° C. for 18 h under N$_2$ protection. The mixture was concentrated and purified via silica gel to afford the crude product, which was re-purified via pre-HPLC to afford the title compound. $^1$H NMR (400 MHz, MeOD) δ 10.10 (s, 1H), 8.34 (d, J=8.8 Hz, 1H), 8.01 (d, J=8.8 Hz, 1H), 7.99 (s, 1H), 5.21 (s, 2H), 3.32 (S, 2H), 3.06-2.94 (m, 4H), 2.61-2.56 (m, 2H), 2.05 (s, 3H), 1.92-1.78 (m, 4H). LC-MS (m/z): 424 [M+H]$^+$.

The following Thallium Flux Assay and/or the Electrophysiology Assays were performed on each of the final product compounds in the Examples unless otherwise noted.

Thallium Flux Assay

A Thallium Flux Assay was performed on the compounds of the Examples. This assay has been described previously; see, e.g., PCT Published Application WO 2013/062900.

Data collected for compounds in the Examples of the present invention using the Thallium Flux Assay are shown in Table 5 below. All of the tested final product compounds in the Examples (diastereomeric mixtures and individual diastereomers) had IC$_{50}$ potencies less than 1 μM in the Thallium Flux Assay.

Electrophysiology Assay

Blocking of Kir1.1 (ROMK1) currents was examined by whole cell voltage clamp (Hamill et. al. Pfluegers Archives 391:85-100 (1981) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% CO$_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066), a non-enzymatic cell dissociation reagent, for approximately 6 min at 37° C. and suspended in 10 mL of bath solution containing (in mM): 150 NaCl, 10 KCl, 2.7 CaCl$_2$, 0.5 MgCl$_2$, and 5 HEPES, at pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 MgCl$_2$, 3 EGTA, and 5 Hepes, at pH 7.4. Electrical access to the cytoplasm was achieved by perforation in 0.13 mg/mL amphotericin B for 4 min. Amphotericin B (Sigma A-4888) was prepared as a 40 mg/mL solution in DMSO.

Voltage protocols and current recordings were performed using the IonWorks HT software/hardware system. Currents were sampled at 1 kHz. There was no correction for liquid junction potentials. The test pulse, consisting of a 100 ms (millisecond) step to 0 mV (millivolts) from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Although not required, a control compound is typically included to support that the assay is giving consistent results compared to previous measurements. The control can be any compound of Formula I of the present invention, preferably with an IC$_{50}$ potency of less than 1 μM in this assay. Alternatively, the control could be another compound (outside the scope of Formula I) that has an IC$_{50}$ potency in this assay of less than 1 μM.

Data collected for compounds in the Examples of the present invention using the Thallium Flux Assay and the Electrophysiology Assay are shown in Table 5 below. All of the tested final product compounds in the Examples (whether diastereomeric mixture or individual diastereomers) had IC$_{50}$ potencies less than 1 μM in one or both of the Thallium Flux Assay and the Electrophysiology Assay.

TABLE 5

| | in vitro potency | |
|---|---|---|
| EXAMPLE # | Thallium Flux IC$_{50}$ (μM) | Electrophysiology IC$_{50}$ (μM) |
| 1 | 0.06838 | 0.033 |
| 2A | 0.03652 | 0.053 |
| 2B | 0.05778 | 0.033 |
| 3A | 0.05487 | 0.017 |
| 3B | 0.05707 | |
| 4A | 0.2669 | |
| 5 | 0.04579 | |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneously hypertensive rats (SHR): Spontaneously hypertensive rats (SHR, male, 6 months, Charles River) were implanted with a DSI TA 11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. Hydrochlorothiazide (HCTZ) (25 mg/kg/day, oral) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Example number 2 was evaluated at oral doses. Once daily (QD) doses at one or more doses within the range of 0.3 to 10 mg/kg resulted in typical reductions in daily (24 h) mean systolic blood pressure ranging from 0.8 to 3.2 kiloPascals (kPa) at the doses used by the last day of the studies.

The Spontaneously Hypertensive Rat Assay is well known and often used in the art as an experimental model simulating human hypertension (see, e.g., Lerman, L. O., et al., *J Lab Clin Med,* 2005; 146:160-173).

While the invention has been described with reference to certain particular embodiments thereof, numerous alternative embodiments will be apparent to those skilled in the art from the teachings described herein. The scope of the claims should not be limited by the specific embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound at the non-specified chiral centers where such forms are possible due to the presence of one or more asymmetric centers. All patents, patent applications and publications cited herein are incorporated by reference in their entirety.

What is claimed is:

1. A compound having structural Formula I:

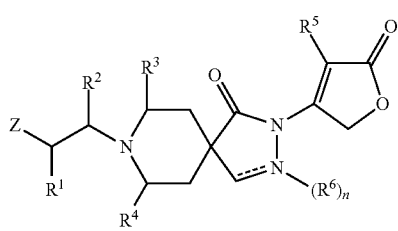

or a pharmaceutically acceptable salt thereof wherein:
$R^1$ is —H, —F, —OH, —$C_{1-3}$alkyl or —$OC_{1-3}$alkyl;
$R^2$ is —H, or $C_{1-4}$alkyl;
$R^3$ is —H, or —$C_{1-3}$alkyl optionally substituted with —OH, —$OCH_3$ or 1 to 3 of —F;
$R^4$ is —H, or —$C_{1-3}$alkyl optionally substituted with —OH, —$OCH_3$ or 1 to 3 of —F;
$R^5$ is —H, halo, —$C_{3-6}$cycloalkyl or —$C_{1-3}$alkyl;
$R^6$ is —H or —$C_{1-3}$alkyl when the dashed bond is absent, or $R^6$ is absent when the dashed bond is a double bond;
n is zero where $R^6$ is absent, or one where $R^6$ is present;
Z is

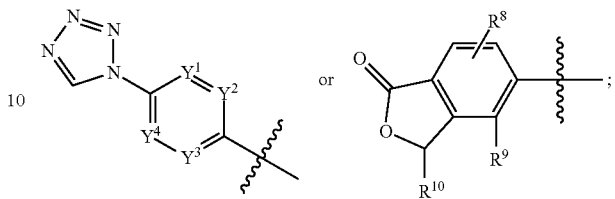

$Y^1$, $Y^2$, $Y^3$ and $Y^4$ are each independently selected from $C(R^7)$ or N;
provided that at most two of $Y^1$, $Y^2$, $Y^3$ and $Y^4$ are N;
each $R^7$ is independently —H, halo, $C_{1-4}$alkyl optionally substituted with 1-3 of —F, or $OC_{1-4}$alkyl;
$R^8$ is —H, halo, or $C_{1-4}$alkyl optionally substituted with 1-3 of —F;
$R^9$ is —H, $C_{1-4}$alkyl optionally substituted with 1-3 of —F, or halo; and
$R^{10}$ is —H or $C_{1-4}$alkyl.

2. The compound of claim 1, or a pharmaceutically acceptable salt thereof, wherein $R^1$ is —H, —F or —OH.

3. The compound of claim 1, or a pharmaceutically acceptable salt thereof, wherein each of $R^3$ and $R^4$ are —H.

4. The compound of claim 1, or a pharmaceutically acceptable salt thereof, wherein $R^6$ is —H or —$C_{1-3}$alkyl.

5. The compound of a claim 1, or a pharmaceutically acceptable salt thereof, wherein $R^6$ is —H.

6. The compound of claim 1, or a pharmaceutically acceptable salt thereof, wherein $R^5$ is —H, —Cl, —$CH_3$ or cyclopropyl.

7. The compound of claim 1, or a pharmaceutically acceptable salt thereof, wherein $R^5$ is —H.

8. The compound of claim 1, or a pharmaceutically acceptable salt thereof, wherein $R^5$ is —$CH_3$.

9. The compound of claim 1 wherein Z is

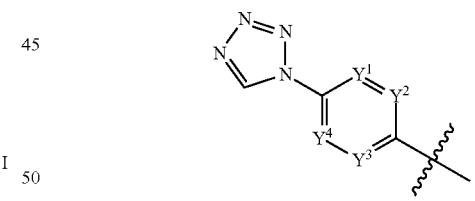

wherein each of the variables $Y^1$, $Y^2$, $Y^3$ and $Y^4$, are as defined in claim 1.

10. The compound of claim 1, or a pharmaceutically acceptable salt thereof, wherein Z is

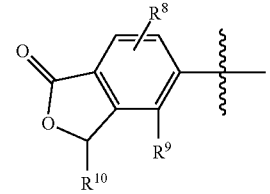

wherein each of the variables $R^8$, $R^9$ and $R^{10}$ are as defined in claim 1.

11. The compound of claim 1, or a pharmaceutically acceptable salt thereof, wherein Z is

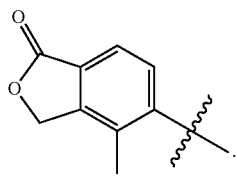 [SMILES: *c1ccc2c(c1C)COC2=O]

12. The compound of claim 1, or a pharmaceutically acceptable salt thereof, of Formula Ia:

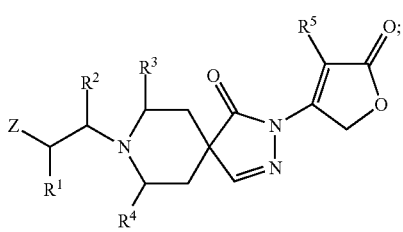

wherein Z, $R^1$, $R^2$, $R^3$, $R^4$, and $R^5$ are as defined therein.

13. The compound of claim 1, or a pharmaceutically acceptable salt thereof, of Formula Ib:

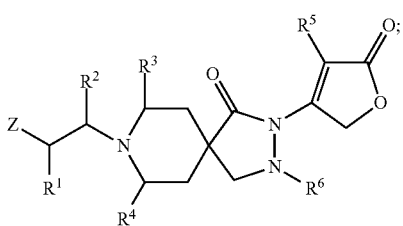

wherein Z, $R^1$, $R^2$, $R^3$, $R^4$, $R^5$, and $R^6$ are as defined therein.

14. A compound which is:
8-(2-hydroxy-2-(4-methyl-1-oxo-1,3-dihydroisobenzofuran-5-yl)ethyl)-2-(4-methyl-5-oxo-2,5-dihydrofuran-3-yl)-2,3,8-triazaspiro[4.5]decan-1-one;
(R)-8-(2-hydroxy-2-(4-methyl-1-oxo-1,3-dihydroisobenzofuran-5-yl)ethyl)-2-(4-methyl-5-oxo-2,5-dihydrofuran-3-yl)-2,3,8-triazaspiro[4.5]decan-1-one;
8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one;
(R)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one;
(S)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]decan-1-one;
8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one;
(R)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one;
(S)-8-(2-(6-(1H-tetrazol-1-yl)pyridin-3-yl)-2-hydroxyethyl)-2-(4-methyl-5-oxo-2,5-dihydrofuran-3-yl)-2,3,8-triazaspiro[4.5]dec-3-en-1-one;
8-(2-(6-(1H-tetrazol-1-yl)pyridazin-3-yl)-2-hydroxyethyl)-2-(4-methyl-5-oxo-2,5-dihydrofuran-3-yl)-2,3,8-triazaspiro[4.5]dec-3-en-1-one;
8-(2-(6-(1H-tetrazol-1-yl)pyridazin-3-yl)ethyl)-2-(4-methyl-5-oxo-2,5-dihydrofuran-3-yl)-2,3,8-triazaspiro[4.5]dec-3-en-1-one;
or a pharmaceutically acceptable salt thereof.

15. A pharmaceutical composition comprising a compound of claim 1 or a pharmaceutically acceptable salt thereof and a pharmaceutically acceptable carrier.

16. The pharmaceutical composition of claim 15 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pro-drug thereof, or a pharmaceutically acceptable salt of any of the foregoing.

17. A method for inhibiting ROMK comprising administering a compound of claim 1 or a pharmaceutically acceptable salt thereof in a ROMK-inhibitory effective amount to a patient in need thereof.

18. A method for causing diueresis, natriuresis or both, comprising administering a compound of claim 1 or a pharmaceutically acceptable salt thereof in a therapeutically effective amount to a patient in need thereof.

19. A method for the treatment of one or more disorders selected from hypertension, acute heart failure, chronic heart failure, pulmonary arterial hypertension, cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, nephrotic syndrome, acute kidney insufficiency, chronic kidney disease, hypercalcemia, Dent's disease, Meniere's disease, or edematous states comprising administering a compound of claim 1 or a pharmaceutically acceptable salt thereof in a therapeutically effective amount to a patient in need thereof.

* * * * *